United States Patent [19]

Williams

[11] 4,428,745
[45] Jan. 31, 1984

[54] FLOW CONTROL MECHANISM FOR A PLASMAPHERESIS ASSEMBLY OR THE LIKE

[75] Inventor: Ronald A. Williams, Mundelein, Ill.

[73] Assignee: Baxter Travenol Laboratories, Inc., Deerfield, Ill.

[21] Appl. No.: 390,464

[22] Filed: Jun. 21, 1982

[51] Int. Cl.³ .............................................. A61M 5/00
[52] U.S. Cl. ....................................... 604/6; 604/250; 604/410; 251/4; 137/883
[58] Field of Search ....................... 604/6, 5, 4, 34, 30, 604/92, 250, 409, 410, 258, 259; 251/4, 6, 7, 9; 137/861, 883

[56] References Cited

U.S. PATENT DOCUMENTS

| | | |
|---|---|---|
| 250,085 | 10/1978 | Tuttle . |
| 1,710,540 | 4/1929 | Hollander . |
| 2,077,774 | 4/1937 | Rudder . |
| 2,261,213 | 11/1941 | Bierman . |
| 2,485,842 | 10/1949 | Pennington . |
| 2,854,027 | 9/1958 | Kaiser et al. . |
| 3,016,915 | 1/1962 | Moeller, Jr. . |
| 3,048,192 | 8/1962 | Murphy, Jr. . |
| 3,157,201 | 11/1964 | Littmann . |
| 3,185,179 | 5/1965 | Harauteneian . |
| 3,187,750 | 6/1965 | Tenczar, Jr. . |
| 3,459,182 | 8/1969 | Naftulin . |
| 3,575,161 | 4/1971 | London . |
| 3,607,082 | 9/1971 | Thiers . |
| 3,610,228 | 10/1971 | Temkin . |
| 3,618,637 | 11/1971 | Santomieri . |
| 3,626,938 | 12/1971 | Versaci . |
| 3,628,813 | 12/1971 | Lee et al. . |
| 3,648,693 | 3/1972 | Koremura . |
| 3,730,170 | 5/1973 | Michael . |
| 3,747,812 | 7/1973 | Karman et al. . |
| 3,782,382 | 1/1974 | Naftulin et al. . |
| 3,783,900 | 1/1974 | Waldbillig . |
| 3,794,032 | 2/1974 | Derouineau . |
| 3,805,842 | 4/1974 | Thompson et al. . |
| 3,834,372 | 9/1974 | Turney . |
| 3,877,428 | 4/1975 | Seagle . |
| 3,886,937 | 6/1975 | Bobo et al. . |
| 3,892,197 | 7/1975 | Kinney et al. . |
| 3,916,948 | 11/1975 | Benjamin . |
| 3,945,380 | 3/1976 | Dabney et al. . |
| 3,957,082 | 5/1976 | Fuson et al. . |
| 3,960,224 | 6/1976 | Silvers . |
| 3,963,024 | 6/1976 | Goldowsky . |
| 3,972,350 | 8/1976 | Pickett . |
| 3,985,134 | 10/1976 | Lissot et al. . |
| 3,994,294 | 11/1976 | Knute . |
| 4,061,142 | 12/1977 | Tuttle . |
| 4,082,095 | 4/1978 | Mendelson et al. . |
| 4,126,133 | 11/1978 | Schwartz . |
| 4,322,298 | 3/1982 | Persidsky ................................ 604/6 |

*Primary Examiner*—Stephen C. Pellegrino
*Attorney, Agent, or Firm*—Paul C. Flattery; Daniel D. Ryan

[57] ABSTRACT

A flow control assembly comprises separate first and second members. The first member is attachable to two or more flexible fluid conduits and serves to establish flow communication between the attached conduits. The second member carries one or more crimping mechanisms and is releasably attachable to the first member. When the first and second members are attached together, the crimping mechanisms of the second member can be independently and selectively operated to close one or more of the flexible conduits attached to the first member. Fluid flow into and through the first member can thus be controlled from a convenient, centralized location. The assembly is extremely adaptable and can be readily incorporated into virtually any fluid system which requires complex, repetitive valving functions. For example, the assembly is ideally suited for use in conjunction with a plasmapheresis system.

28 Claims, 14 Drawing Figures

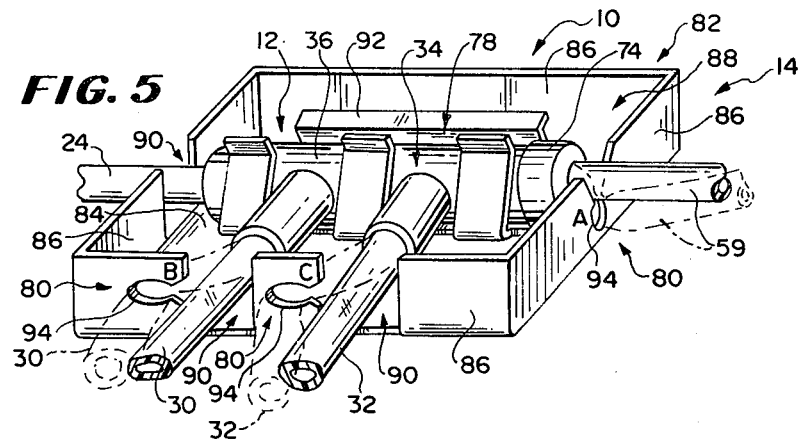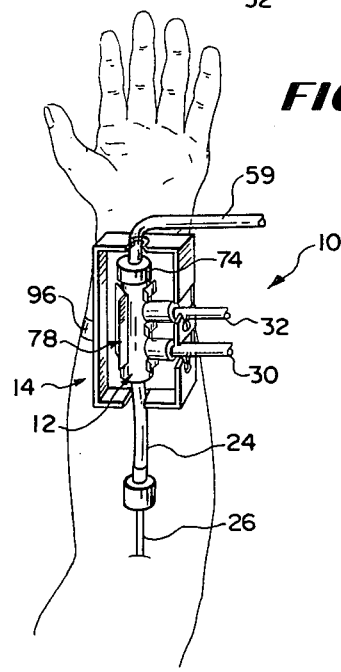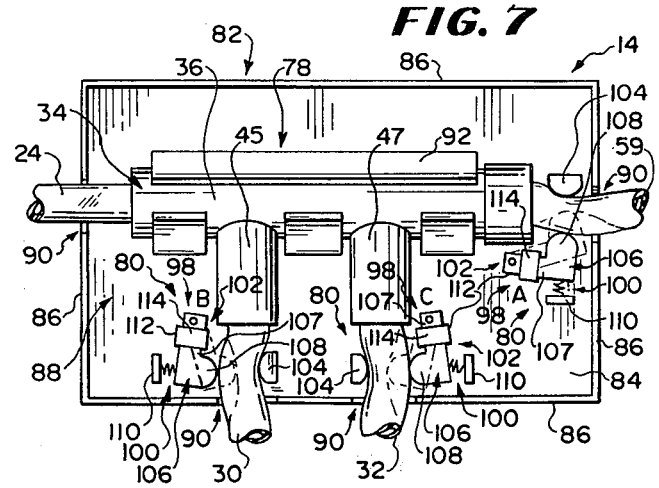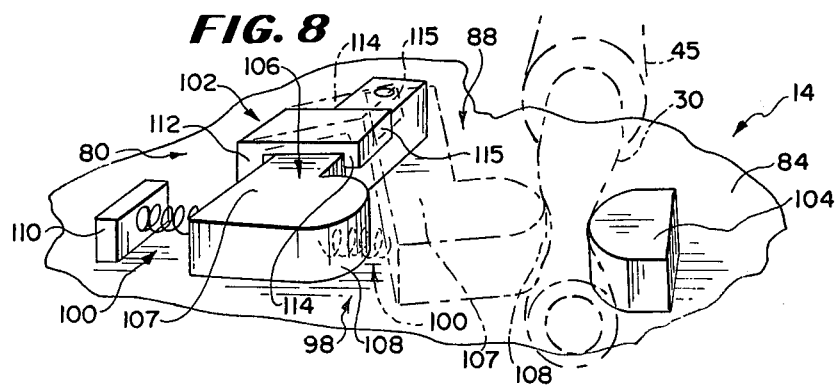

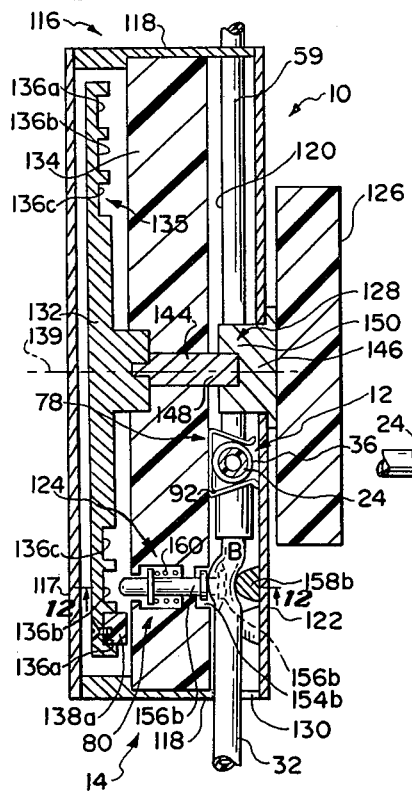
FIG. 11
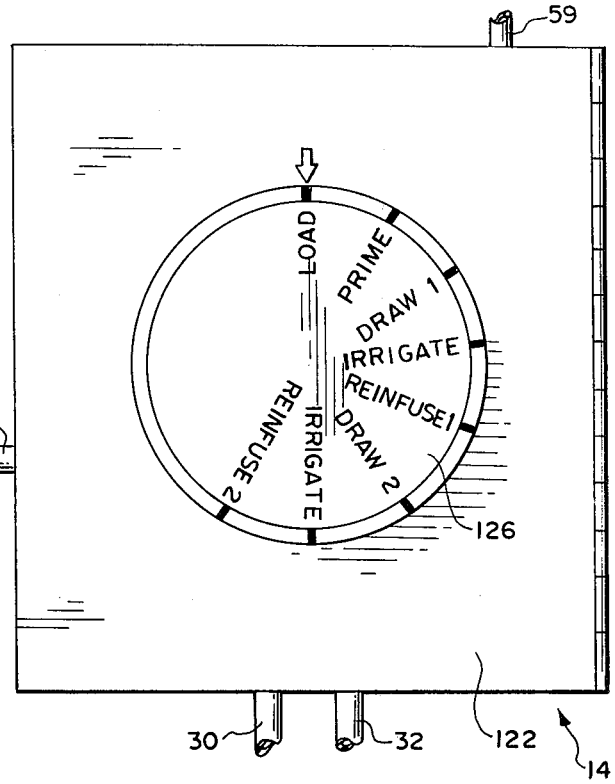
FIG. 13
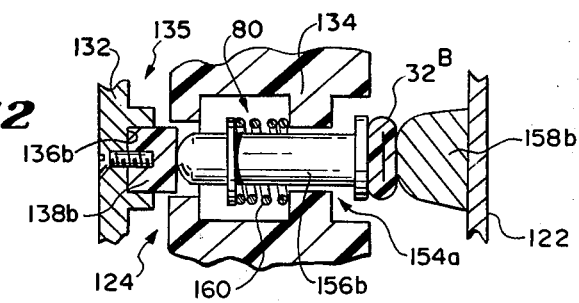
FIG. 12
FIG. 14
| POSITION | CRIMPING MEANS | | |
|---|---|---|---|
|  | A | B | C |
| PRIME | O | X | X |
| DRAW 1 | X | O | X |
| IRRIGATE | O | X | X |
| REINFUSE 1 | O | X | X |
| DRAW 2 | X | X | O |
| IRRIGATE | O | X | X |
| REINFUSE 2 | O | X | X |
OPEN  O
CLOSED  X

FLOW CONTROL MECHANISM FOR A PLASMAPHERESIS ASSEMBLY OR THE LIKE

FIELD OF THE INVENTION

The invention generally relates to fluid control devices. The invention also generally relates to plasmapheresis apparatus and processes.

BACKGROUND AND OBJECTS OF THE INVENTION

Plasmapheresis is a procedure which facilitates the collection of source plasma for commerical fractionation into antihemophiliac factor (AHF), albumin, and other plasma protein fractions. During conventional plasmapheresis, a unit of whole blood is collected and separated into red cells and plasma. The red cells are returned to the donor, and the plasma is retained for fractionation purposes. Another unit of whole blood is then drawn from the donor utilizing the same phlebotomy, and the whole blood is again separated into red cells and plasma. As before, the red cells are returned to the donor, and only the plasma is retained. The end result is, for each plasmapheresis procedure, two units of source plasma for fractionation purposes.

Representative examples of disposable plasmaphersis assemblies include the following U.S. Pat. Nos.:

Naftulin 3,459,182
Naftulin et al 3,782,382
Dabney 3,945,380

Representative examples of known, commercially available disposable plasmapheresis assemblies include those sold by Fenwal Laboratories (a division of Travenol Laboratories, Inc., Deerfield, Ill.); Cutter laboratories, Inc., (Berkely, Ca.); Delmed (Irvine, Ca.); and Terumo Company, Ltd., (Japan).

The nature of a typical plasmapheresis procedure demands the use of clamping devices which selectively channel and control the flow of blood and components through a given plasmapheresis assembly. Typically, several manually actuated clamping devices, such as hemostats and/or roller clamps, are used in tandem for this purpose. Use of such devices entails multiple clamping arrangements and time consuming manipulations during the procedure. The devices also introduce the possibility of operator error.

The plasmapheresis assembly discussed in the above-cited Naftulin et al document uses a manifold to interconnect the blood collection containers with the needle. The flow of fluids through the manifold is controlled by the use of inline ball valves. Such an inline valving arrangement, however, does not facilitate repetitive valving functions, because, once a ball valve is squeezed out of the fluid path to open flow communication, it cannot be easily returned to subsequently close flow communication. Furthermore, such an inline valving arrangement introduces a potentially leak-prone device into the flow paths of the assembly; could be prone to producing blood clots; and adds yet another material in contact with the blood.

It is one of the principal objects of this invention to provide a fluid control assembly which performs complex, repetitive valving operations to establish a plurality of flow modes in a given fluid circuit, such as a plasmapheresis assembly, without introducing complicated and/or leak-prone devices into the fluid circuit.

It is another one of the principal objects of this invention to provide a fluid control assembly which can be utilized to control the flow of fluids through a given fluid circuit, such as a plasmapheresis assembly, from a convenient centralized location, thereby simplifying, as much as possible, the manipulations required during the operation of the fluid circuit, and thereby minimizing, as much as possible, the chance of operator error.

It is yet another one of the principal objects of this invention to provide a fluid control assembly which can be readily incorporated into any given fluid circuit, including one utilized for plasmapheresis, without entailing major modifications to the circuit.

SUMMARY OF THE INVENTION

To achieve these and other objects, the invention provides a flow control assembly for flexible fluid conduits. The assembly comprises first means which is attachable to two or more flexible fluid conduits and which establishes flow communication between the attached conduits. The assembly also comprises second means which is releasably attachable to the first means. When the first and second means are attached together, the second means is operative for selectively crimping at least one of the conduits attached to the first means. Fluid flow through the first means can thus be selectively controlled by the operator.

In one embodiment, the second means includes a compact, lightweight frame having a base and sidewalls which together define an interior area. The frame, if desired, could be constructed so as to be conveniently worn on the wrist of the donor. In this embodiment, attachment means is provided for releasably attaching the first means within the confines of the interior area. The sidewalls include openings which correspond in number with the number of flexible conduits associated with the first means. The openings are situated to accommodate the unimpeded passage of the fluid conduits from the first means outwardly beyond the interior area of the frame.

In one embodiment, the second means includes a notch associated with one or more of the openings. Each notch can selectively receive and crimp a portion of the flexible conduit which passes through the opening.

In one embodiment, the second means includes at least one clamping means which is situated on the base of the frame intermediate the attachment means and a facing sidewall. The clamping means is operative for movement between a first, or opened, position, which is generally spaced away from a selected one of the conduits associated with the first means, and a second, or closed, position, which presses against and collapses the one conduit.

In one embodiment, the clamping means is biased toward the second, or closed, position. In this arrangement, the assembly further includes means for releasably locking the clamping means in the first, or opened, position against the action of the biasing means.

In one embodiment, the second means includes a housing having spaced walls defining an interior area and a door which is movable between an opened position permitting access into the interior area and a closed position blocking the access. In this embodiment, the attachment means is carried within the interior area of the housing. Also carried within the interior of the housing is fluid control means which is operative for selectively crimping at least one of the conduits attached to the first means. Movable control handle means is carried by the door, and linkage means operatively connects the control handle means with the fluid control means when the door is in the closed position. The fluid control means can thus be operated in response to movement of the control handle to control fluid flow through the first means.

The invention also provides a plasmapheresis assembly which includes the flow control assembly as above generally described. In this operative environment, the first means of the flow control assembly takes the shape of a manifold which interconnects a pair of blood collection containers with a primary conduit having, at one end, a phlebotomy needle. In this arrangement, the manifold is releasably attachable to the second means. When so attached, the flow control assembly serves to selectably and individually control the fluid flow between the phlebotomy needle and each of the blood collection containers during the course of the plasmapheresis procedure.

The fluid control assembly which embodies the features of the invention can handle complex, repetitive valving functions and does not constitute a leak-prone device disposed in the flow path. Indeed, the assembly is so straightforward in construction and operation that it can be readily incorporated into virtually any fluid system with only minimal modifications to the system.

Other features and advantages of the invention will be pointed out in, or will be apparent from, the specification and claims, as will obvious modifications of the embodiments shown in the drawings.

DESCRIPTION OF THE DRAWINGS

FIG. 5 is an enlarged perspective view of the fluid control assembly shown in FIG. 4, with the manifold and the housing attached together;

FIG. 6 is a view of the flow control assembly shown in FIG. 5 strapped on the wrist of a donor;

FIG. 7 is a plan view of another embodiment of a flow control assembly which embodies various features of the invention;

FIG. 8 is an enlarged perspective view of a portion of the flow control assembly shown in FIG. 7;

FIG. 11 is a section view of the flow control assembly taken generally along line 11—11 of FIG. 9;

FIG. 12 is a enlarged view of a portion of the flow control assembly taken generally along line 12—12 in FIG. 11 with the pin means actuated to crimp the associated tubing;

FIG. 13 is a front plan view of the flow control assembly shown in FIG. 9 with the door closed; and FIG. 14 is a table showing the relative positions of the valve members associated with a fluid flow control assembly which embodies the features of the invention during the course of a typical plasmapheresis procedures.

Before explaining the embodiments of the invention in detail, it is to be understood that the invention is not limited in its application to the details of construction and the arrangement of components as set forth in the following description or as illustrated in the accompanying drawings. The invention is capable of other embodiments and of being practiced or carried out in various ways. Furthermore, it is to be understood that the phraseology and terminology employed herein is for the purpose of description and should not be regarded as limiting.

DESCRIPTION OF THE PREFERRED EMBODIMENTS

Figure 1:
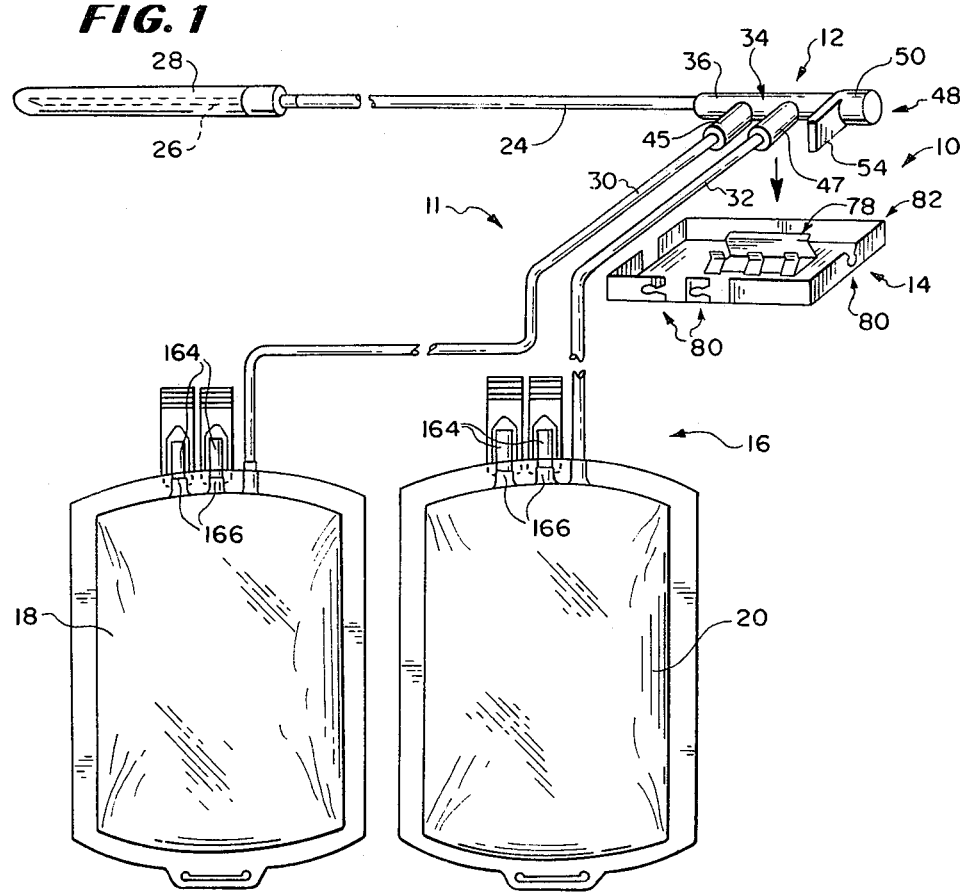
FIG. 1 is a partially perspective view of a plasmapheresis assembly which includes a flow control assembly which embodies various features of the invention.

A flow control assembly 10 which embodies various of the features of the invention is shown in FIG. 1.

Generally, as shown in FIG. 1, the assembly 10 includes first means 12 which can be readily incorporated into a fluid flow network 11 having two or more flexible fluid conduits. When part of the network 11, the first means 12 serves to establish flow communication between the attached flexible conduits of the network 11.

Use of the term "flexible" herein signifies that the conduit or tubing has resiliently deformable sidewalls which can be pinched or crimped together in response to an external force, thereby occluding and closing the fluid path through the conduit or tubing, and which are capable of resiliently returning to a normally open position when the external force is removed.

The assembly 10 also includes second means 14 which constitutes an element which is physical separate from the first means 12, but which can be releasably attached to the first means 12 when desired.

As will be described in greater detail later herein, when the first and second means 12 and 14 are attached together, the second means 14 is operative for selectively exerting an external force to crimp or collapse at least one of the flexible conduits attached to the first means 12. The flow of fluids into and through the first means 12, and thus through the entire network 11, can thereby be controlled from a convenient, centralized located.

It will be appreciated that the fluid control assembly 10 of this invention can be readily incorporated into virtually any fluid network 11. However, the detailed description of the fluid control assembly 10 which follows will be made in the context of its use in association with a plasmapheresis assembly 16. Nevertheless, the adaptability of the fluid control assembly 10 for use in diverse other operative environments should be kept in mind.

As shown in FIG. 1, the plasmapheresis assembly 16 includes first and second whole blood collection containers, respectively 18 and 20. The containers 18 and 20 each typically takes the form of a bag fabricated from a plastic material, such as plasticized medical grade polyvinyl chloride.

The fluid network 11 of the plasmapheresis assembly 16 serves to conduct blood and other parenteral fluids into and between the containers 18 and 20. In this operative environment, the fluid network 11 includes lengths of flexible tubing, also fabricated from medical grade polyvinyl chloride plastic.

In the illustrated embodiment, and still referring principally to FIG. 1, the fluid network 11 of the plasmapheresis assembly 16 includes a length of flexible tubing 24. This length of tubing 24 will hereafter be referred to as the primary tubing of the assembly 16.

A phlebotomy needle 26 is attached in flow communication with one end of the primary tubing 24. A removable needle cover 28 of conventional construction (see, for example, Bellamy Jr., U.S. Pat. No. 3,123,072) normally seals the needle 26 from communication with the atmosphere until venipuncture is made.

The fluid network 11 also includes first and second auxiliary tubings, respectively 30 and 32, which communicate with the containers 18 and 20.

The flow control assembly 10 which forms a part of the plasmapheresis assembly 16 may be variously constructed. In the illustrated embodiment, the first means 12 of the control assembly 10 takes the form of a manifold 34 which serves to interconnect both of the containers 18 and 20 in flow communication with the phlebotomy needle 26. The manifold 34 itself may be variously constructed. However, in the illustrated embodiment, the manifold 34 is generally constructed along the lines disclosed in copending Nevens et al, U.S. patent application Ser. No. 300,338, filed Sept. 8, 1981, now U.S. Pat. No. 4,407,660, and entitled PLASMAPHERESIS ASSEMBLY AND ASSOCIATED FLUID MANIFOLD.

Figure 2:
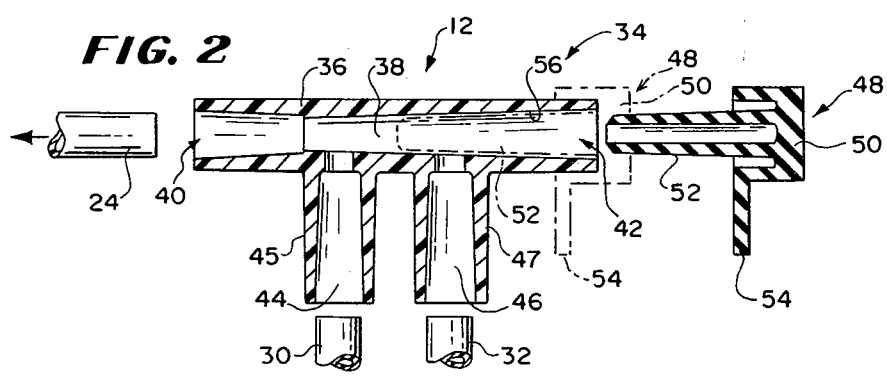
FIG. 2 is an enlarged and exploded section view of the manifold which is associated with the flow control assembly shown in FIG. 1.

More particularly, and as can best be seen in FIG. 2, the manifold 34 includes a tubular main body 36 through which a main passage 38 extends. The main passage 38 has axially spaced first and second end portions 40 and 42.

Still referring principally to FIG. 2, a pair of branch passages 44 and 46 communicates with the main passage 38. One branch passage 44 (hereafter referred to as the first branch passage) is disposed generally adjacently to the end portion 40. The other branch passage 46 (hereafter referred to as the second branch passage) is disposed generally adjacently to the other end portion 42.

In the illustrated embodiment, each branch passage 44 and 46 extends within a tubular body, respectively 45 and 47. The tubular bodies 45 and 47 extend in a spaced-apart, parallel fashion outwardly from the same side of the main body 36.

The manifold 34 as heretofore described lends itself to relatively efficient and economical manufacturing techniques. For example, in the illustrated embodiment, the main body 36 and tubular bodies 45 and 47 of the manifold 34 are injection molded as an integral unit from a rigid or semi-rigid plastic material, such as polycarbonate, polyvinyl chloride, or acrylic.

The manifold 34 further includes plug means 48 which is removably insertable into the end portion 42 of the main passage 38, as is shown in solid lines in FIG. 1 and in phantom lines in FIG. 2.

In the illustrated embodiment, the plug means 48 includes a cap portion 50, which is formed to fit snugly in a fluid-tight relationship about the exterior of the end portion 42, and a stem portion 52, which is formed to extend axially into and in a fluid-tight relationship within the main passage 38. In the illustrated and preferred embodiment, the cap portion 50 includes a tab 54 which can be grasped between the fingers of the operator to facilitate removing the cap portion 50 from its snug engagement on the end portion 42.

In the illustrated and preferred embodiment, the main passage 30 includes an axially inwardly tapered portion 56. The stem portion 52 of the plug means 48 is correspondingly tapered to promote the desired fluid-tight fit.

The plug means 48 can be fabricated by injection molding from a rigid or semi-rigid plastic material, such as polycarbonate, polyvinyl chloride, or acrylic. Alternately, the plug means 48 can be made utilizing a compression molding process from a resiliently compressible material, such as natural rubber. This latter construction is preferred because it further promotes the tight, interference fit of the stem portion 52 within the main passage portion 38 and of the cap portion 50 about the end portion 42.

As can be seen in FIGS. 1 and 2, the end of the primary tubing 24 opposite to the phlebotomy needle 26 is bonded, such as by solvent sealing, within the end portion 40 of the manifold main passage 38. Likewise, the first and second auxiliary tubings 30 and 32 are also attached, such as by solvent sealing, in flow communication with the first and second branch passages 44 and 46 of the manifold 34. The manifold 34 thus interconnects the collection containers 18 and 20 with the phlebotomy needle 26.

As is best shown in phantom lines in FIG. 2, when the plug means 48 is positioned on the end portion 42 of the main passage 38, the cap portion 50 sealingly closes the end portion 42, and the stem portion 52 sealingly closes the second container 20 from communication with the main passage 38. However, at the same time, communication between the first container 18 and the main passage 38 is unimpeded.

The plug means 48, when so positioned, serves to prevent the loss or intermixing of anticoagulant solution (not shown), which is typically provided in measured amounts in each container 18 and 20 to prevent blood clotting during the plasmapheresis procedure. The plug means 48 thus retains the desired amount of anticoagulant solution in each container 28 and 20 prior to the commencement of the plasmapheresis procedure.

Figure 3:
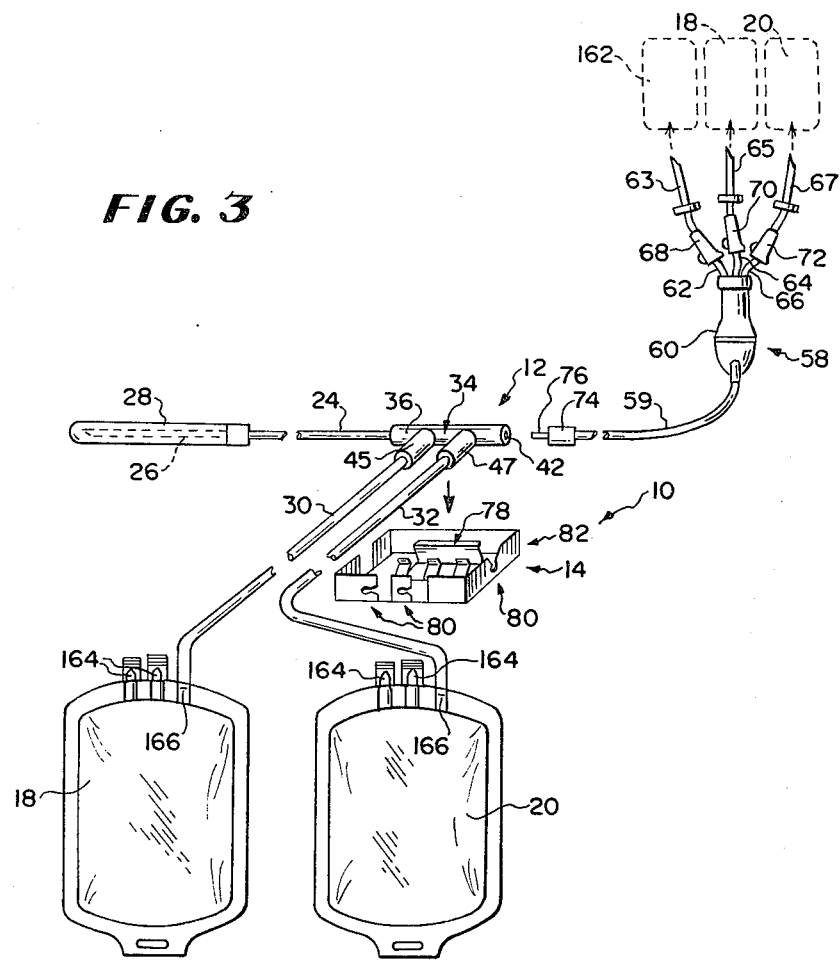
FIG. 3 is a partially perspective view of the plasmapheresis assembly shown in FIG. 1, with the plug member associated with the manifold removed so that a recipient set can be coupled to the assembly.

As can be seen in FIG. 3, the plug means 48 can be removed, when desired, to accommodate the connection of a recipient set 58 or the like to the plasmapheresis assembly 16. As will be described in greater detail later, the recipient set 58 allows the introduction of saline and the return of some of the components collected during the course of the plasmapheresis procedure.

The recipient set 58 can be variously constructed. However, in the illustrated embodiment (see FIG. 3), the set 58 includes a length of flexible tubing 59 and an inline combination filter and drip chamber 60. Upstream of the filter/drip chamber 60 are three individual inlet lines 62, 64, and 66, each having a spiked end portion, respectively 63, 65, and 67. Roller clamps 68, 70, and 72 are provided inline with the inlet lines 62, 64, and 66 to control the fluid flow therethrough.

The tubing 59 of the recipient set 58 is connected to the end 42 of the main passage 38 by means of a coupling member 74. The coupling member 74 is fabricated to include a tapered end portion 76 which, like the tapered stem portion 52 of the plug means 48, is insertable into an interference fit relationship into the main passage 38 through the end portion 42. However, unlike the stem portion 52, the end portion 76 of the coupling member 74 is purposefully sized to occupy only a part of the inwardly tapered portion 56 of the main passage 38 intermediate the junction of the second branch passage 46 and the end portion 42.

Reference is now made to the second means 14 of the control assembly 10 which is associated with the plasmapheresis assembly 16. In this operative environment (see FIGS. 1 and 3), the second means 14 includes means 78 for releasably attaching to the manifold 34 to the second means 14. The second means 14 also includes means 80 which is operative, when the manifold 34 is attached, for individually and selectively exerting an external force to crimp or collapse each of the auxiliary conduit tubings 30 and 32. Fluid communication between the primary conduit tubing 24 and each of the blood collection containers 18 and 20 can thus be controlled by the device 10. As shown in FIG. 3, the crimping means 80 can also be provided, if desired, to selectively crimp or collapse the flexible tubing 59 which is associated with the recipient set 58.

The second means 14 as just described may be variously constructed. Three representative embodiments of the second means 14 are shown, respectively, in FIGS. 4 through 6, FIGS. 7 and 8, and FIGS. 9 through 13.

Figure 4:
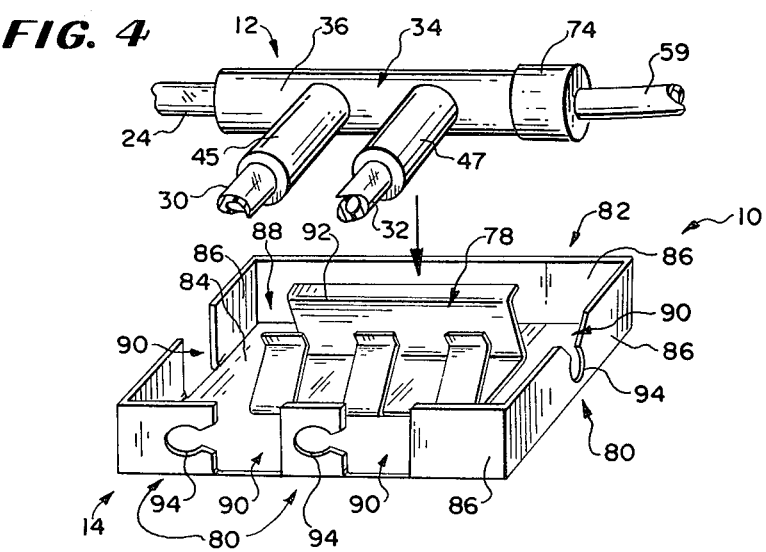
FIG. 4 is an enlarged perspective view of the fluid control assembly shown in FIG. 1 with the manifold and housing in a separated relationship.

Reference is first made to the embodiment shown in FIGS. 4 through 6. In this embodiment, which is also generally shown in FIGS. 1 and 3, the second means 14 includes a compact, portable frame 82 which includes a base 84 and four upstanding sidewalls 86 which, together with the base 84, define an interior area 88.

The second means 14 shown in FIGS. 4 through 6 may be constructed out of a lightweight rigid plastic material utilizing injection molding techniques. It may also be formed of a lightweight metal.

As is shown in FIG. 6, because of its compact size, the second means 14 may include a strap 96 attached to the underside of the base 84, so that the frame 82 can be conveniently worn on the arm of the donor. Alternately, the frame 82 could be either temporarily or permanently attached to a suitable support frame (not shown) in the vicinity of the donor.

In this embodiment, the attachment means 78 comprises a resilient spring clip 92 which is configured to engage the manifold 34 in a releasable snap fit, as can be seen in FIGS. 5 and 6. The spring clip 92 may be a integrally molded part of the frame 82, or the clip 92 may comprise a separate piece bolted, glued, or otherwise attached to the base 84 of the frame 82.

Selected sidewalls 86 of the frame 82 preferably include means defining openings 90 which correspond in number with the number of flexible conduits attached to the manifold 34. Accordingly, in the illustrated embodiment, four openings 90 are provided. The openings 90 are situated relative to the manifold 34, when the manifold 34 is properly attached to the frame 82, so as to accommodate an unimpeded, generally straight-line passage of the tubings 24, 30, 32, and 59 from the manifold 34 outwardly beyond the frame 82 (see FIGS. 5 and 6). Preferably, as is shown in FIG. 4, the plug means 48 is removed and the recipient set 58 attached to the manifold 34 prior to attachment of the manifold 34 to the frame 82.

In this embodiment, the crimping means 80 takes the form of a generally elongated notch 94 associated with selected openings 90. Each notch 94 is operative for selectively receiving and thereby crimping or collapsing a portion of the tubing which passes through the associated opening 90.

More particulary, as best shown in FIGS. 4 and 5, the notch 94 is associated with the openings 90 through which the auxiliary tubings 30 and 32 and the recipient set tubing 59 pass. The notch 94 may be generally horizontally disposed along the side of the opening 90, as shown with the notch 94 associated with the auxiliary tubings 30 and 32. Alternatively, the notch 94 may be generally vertically disposed within the opening 90, as shown with the notch 94 associated with the recipient set tubing 59.

In either configuration, when any one of the tubings 30, 32, or 59 is disposed out of engagement within its associated notch 94 (as shown in solid lines in FIG. 5) fluid flow is permitted through the disengaged tubing. When any one of the tubings 30, 32, or 59 is engaged within its associated notch 94 (as shown in phantom lines in FIG. 5), the engaged flexible tubing 30, 32, and 59 is pinched or crimped, closing the fluid path through the crimped tubing.

Each of the tubings 30, 32, and 59 can be individually and repeatedly placed into and out of engagement with the associated notch 94 as desired, with very little effort and manipulation.

Reference is now made to the alternate embodiment of the second means 14 shown in FIGS. 7 and 8. The second means 14 in this embodiment shares several of the features of the second means 14 shown in FIGS. 4 through 6. These common features are assigned the same reference numerals.

As in the FIGS. 4 through 6 embodiment, the second means 14 in FIGS. 7 and 8 includes a frame 82 having a base 84 and four upstanding sidewalls 86 which collectively define an interior area 88. The attachment means 78 also takes the form of a resilient spring clip 92 disposed within the interior area 88 to releasably receive the manifold 34. Openings 90 are also formed along the sidewalls 86 to accommodate passage of the primary tubing 24, the auxiliary tubings 30 and 32, and the recipient tubing 59.

However, instead of utilizing the notches 94 provided in the FIGS. 4 through 6 embodiment, in FIGS. 7 and 8, the crimping means 80 takes the form of clamping means 98 which are carried on the base 84 within the confines of the interior area 88 intermediate the spring clip 92 and the facing sidewalls 86. The clamping means 98 are in general operative alignment with the openings 90 associated with the auxiliary tubing 30 and 32 and the recipient set tubing 59.

The clamping means 98 are selectively operative for movement between a first, or opened, position (shown in solid lines in FIGS. 7 and 8), which is generally spaced away from the associated tubing, and a second, or closed, position (shown in phantom lines in FIGS. 7 and 8), which presses against and collapses, or occludes, the associated tubing.

Preferably, the clamping means 98 includes means 100 for biasing the clamping means 98 toward the second, or closed, position. In this preferred arrangement, the clamping means 98 also includes means 102 for releasably locking the clamping means 98 in the first, or opened, position against the action of the biasing means 100.

Alternately, the clamping means 98 could be unbiased or biased toward the first, or opened, position. In this arrangement (not shown), the locking means 102 would serve to lock the clamping means 98 in the second, or closed, position.

The clamping means 98 as just described may be variously constructed. As shown in FIGS. 7 and 8, the clamping means 98 includes a fixed member 104 and a movable member 106. The movable member 106, in turn, includes a body 107 (see, in particular, FIG. 8) and an occluder tip portion 108. The member 106 is movable relative to the fixed member 104 between the heretofore described first and second positions.

When the movable member 106 is in the heretofore discussed first, or opened, position (shown in solid lines in FIGS. 7 and 8), the occluder tip portion 108 of the movable member is disposed away from the fixed member 104. Free, unoccluded passage of the tubing between the tip portion 108 and the fixed member 104 is thereby permitted (see, in particular FIG. 8).

When the movable member 106 is in the second, or closed, position (shown in phantom lines in FIG. 8), the occluder tip portion 108 is disposed adjacent to the fixed member 104. Tubing which passes between the fixed member 104 and the tip portion 108 is occluded or collapsed between the occluder tip 108 and the member 104 (again see, in particular, FIG. 8).

In this embodiment, the biasing means 100 takes the form of a spring which extends between a support pedistal 110 (see FIG. 7) and the body 107 of the movable member 106. The spring 100 serves to bias the movable member 106 toward the fixed member 104, and thus toward the second, or closed, position.

In this embodiment, the locking means includes a resilient upstanding member 112 attached to the base 84. The member 112 includes a tab 114 which overhangs the body 107 of the moveable member 106. The tab 114 has a hooked end portion 115 which (as shown in solid lines in FIG. 8) is normally biased toward an engaged position with the body 107 when the movable member 106 is disposed in its first, or opened, position. The member 112 thereby retains the movable member 106 in this position against the biasing force of the spring 100. However, the tab 114 can be resiliently moved away from its engaged position (as shown in phantom lines in FIG. 8), thereby releasing the body 107 to allow the return of the movable member 106 toward the fixed member 104 in response to the spring 100.

As in the first described embodiment, operation of the movable members 106 can thus be independently and selectively accomplished by the operator with little effort and manipulation.

As in the first described embodiment, the frame 82 may be made of lightweight plastic and/or metal materials and be sized so as to be worn on the arm of the donor. The associated clamping means 98 may also be of plastic material or the like.

Attention is now directed to the third alternate embodiment shown in FIGS. 9 through 13. In this embodiment, the second means 14 includes a housing 116 having a rear wall 117 and spaced sidewalls 118 which define an interior area 120. A door 122 is connected by a hinge 119 (see FIG. 9) to one of the walls 118 and is movable between an opened position (shown in FIG. 9), permitting access into the interior area 120, and a closed position (shown in FIGS. 11 and 13) blocking the access.

In this embodiment, the attachment means 78 takes the form of the heretofore described resilient spring clip 92 (see FIGS. 9 and 11) located within the interior area 120 for releasably securing the manifold 34 within the confines of the interior area 122.

In this embodiment, the crimping means 80 includes fluid control means 124 which is also carried within the interior area 120 and which is operative for selectively crimping at least one of the tubings associated with the manifold 34. The crimping means 80 also includes movable control handle means 126 (as best shown in FIGS. 11 and 13) carried by the door 122.

In this arrangement, the crimping means 80 further includes linkage means 128 (see FIGS. 9 and 11) which operatively connects the control handle means 126 with the fluid control means 124 when the door 122 is in its closed position. As will be described in greater detail later herein, movement of the control handle means 126 thereby serves to operate the fluid control means 124 to control fluid flow through the manifold 34.

While the fluid control means 124 shown in FIGS. 9 through 13 may be variously constructed, in the illustrated embodiment, the control means 124 is constructed along the lines disclosed in copending Bilstad et al, U.S. patent application Ser. No. 347,819, entitled Control System for Fluid Flow Apparatus, which is a continuation of U.S. patent application Ser. No. 139,884, filed Apr. 14, 1980 (now abandoned).

More particularly, the housing 116 includes an interior wall 134 (see, in particular, FIG. 11) which partitions the interior area 120 of the housing 116. As is best shown in FIGS. 9 and 11, the spring clip 92 is carried on the front side of the wall 134 (i.e., the side facing the door 122).

Figure 9:
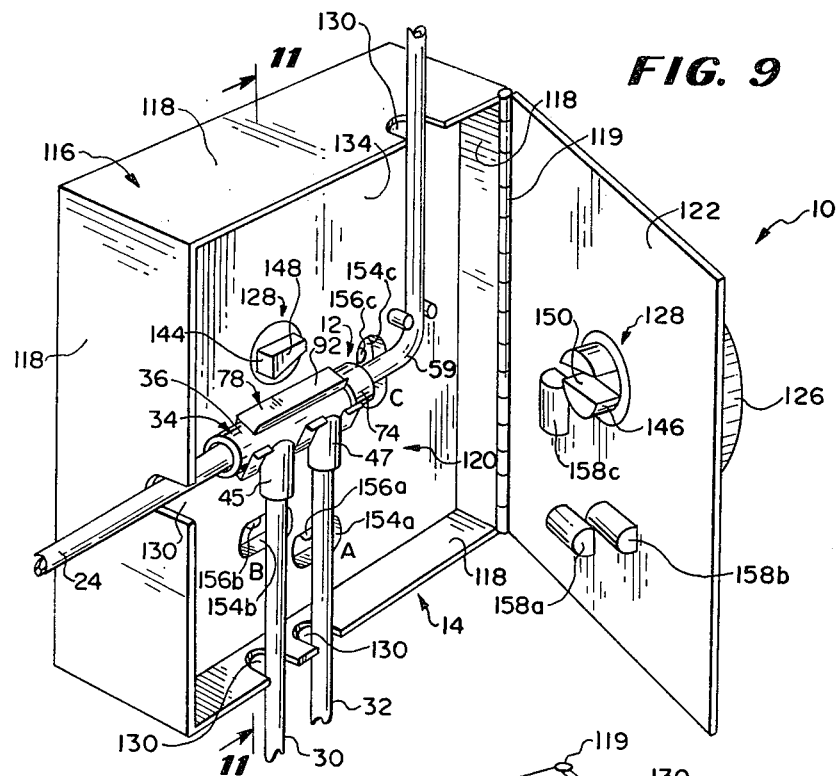
FIG. 9 is a front perspective view of another embodiment of a flow control assembly which embodies various features of the invention.

As best shown in FIG. 9, openings 130 are formed in preselected areas of the walls 118 of the housing 116. The openings 130, like the openings 90 in each of the heretofore described embodiments, are arranged relative to the manifold 34 to accommodate the desired unimpeded, generally straight-line passage of the tubings 24, 30, 32, and 59 from the manifold 34 outwardly beyond the housing 116.

Figure 10:
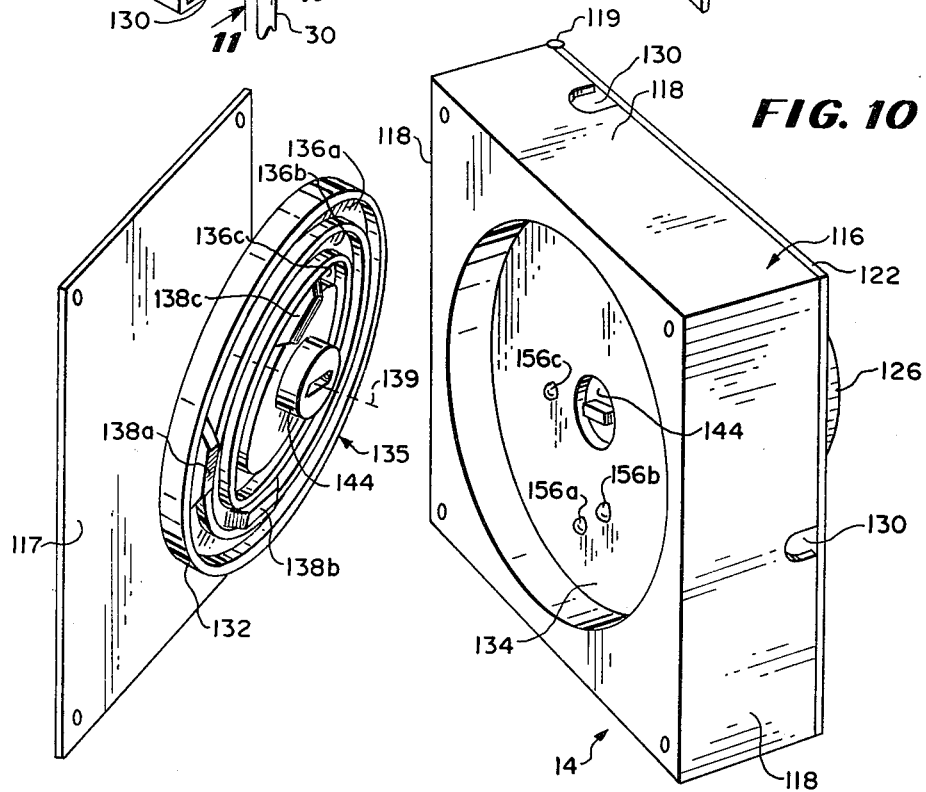
FIG. 10 is an exploded perspective view of the rear of the flow control assembly shown in FIG. 9.

In this arrangement, the fluid control mears 124 includes a cam plate 132 (see FIGS. 10 and 11) which is positioned between the back side of the wall 134 (i.e., the side facing away from the door 122) and the rear wall 117 of the housing 116. As is best shown in FIG. 10, the cam plate 132 includes a generally flat surface 135 which faces the back side of the wall 134. The surface 135 includes a series of concentric, annular grooves 136 which are disposed at different radii from the axis of rotation 139 of the cam plate 132. The number of grooves 136 can vary according to the desired operation of the assembly 10. In the illustrated embodiment (see FIG. 10), three groves 136a, b, and c are provided.

The grooves 136a, b, and c receive separate, preferably generally arcuate cam members 138. The number of cam members 138 attached to the grooves 136a, b, and c can vary according to the desired operation of the assembly 10. In the illustrated embodiment, three cam member, designated 138a, b and c, are shown. The cam member 138a is disposed in the outermost groove 136a, the cam member 138c is disposed in the innermost groove 136c, and the cam member 138b is disposed in the intermediate groove 136b.

The linkage means 128 includes a pair of separable shaft members 144 and 146. As is best shown in FIG. 11, the shaft member 144 is coupled to the cam plate 132 to affect rotation of the cam plate 132 about its axis 139. The shaft member 146 is coupled to the control handle means 126 for rotation in response to movement of the control handle means 126.

As best shown in FIG. 9, the separate shaft members 144 and 146 define, at their facing ends, V-shaped, mating portions, respectively 148 and 150. The portions 148 and 150 permit the operative connection of the shaft members 144 and 146, but only when the door 122 is in its closed position and the members 144 and 146 each occupies one specific relative rotational position to bring the portions 148 and 150 into mating alignment (see FIG. 11).

Accordingly, when the door 122 is in its opened position, the manifold 34 can be releasably secured into the position shown in FIG. 9, with the primary tubing 24, the auxiliary tubings 30 and 32, and the recipient tubing 59 extending through the openings 130 provided.

If control handle means 126 is in its specific rotational position relative to the cam plate 132, the door 122 can be successfully closed and the members 148 and 150 mated. Otherwise, the members 148 and 150 will not mate, and the door 122 cannot be closed.

Once the door 122 is closed, the control handle means 126 is operatively connected with the cam plate 132. Rotation of the control handle means 126 will rotate the cam plate 132 and move the attached cam members 138a, b, and c, in arcuate paths about the axis 139.

As is best shown in FIG. 9, the fluid control means 124 further includes apertures 154 formed at preselected positions in the wall 134. The number of apertures 154 can vary according to the desired operation of the assembly 10. In the illustrated embodiment, three apertures, designated 154a, b and c, are provided in the wall 134. In this arrangement, the apertures 154a, b, and c are purposefully disposed along the path, respectively, of the tubings 32, 30, and 59 as they extend between the manifold 34 and the openings 130.

The apertures 154a, b, and c are also purposefully disposed at different radii from the rotational axis 139 of the cam plate 132 so as to lie in the path of arcuate travel of, respectively, the cam members 138a, b, and c.

The fluid control means 124 also includes pin means 156 carried within each aperture 154a, b, and c. The pin means 156 are therefore correspondingly designated 156a, b, and c. Furthermore, anvil members 158 are carried at preselected locations on the interior of the door 122. The anvil members 158 correspond in number and alignment with the pin means 156a, b, and c and are therefore correspondingly designated 158a, b, and c (see FIG. 9).

As can be seen in FIG. 11, when the door 122 is in its closed position, the tubing 32, 30, and 59 will be situated between the associated pin means 156a, b, and c and the associated anvil member 158a, b and c.

Each of the pin means 156a, b, and c is movable between a normal position (shown in solid lines in FIG. 11) and a displaced position (shown in phantom lines in FIG. 11 and in solid lines in FIG. 12). As can best be seen in FIG. 12, movement of the pin means 156a, b, and c from its normal position toward its displaced position presses the associated tubing 32, 30, and 59 between the associated pin means 156a, b, and c and the associated anvil member 158a, b, and c. An area of the tubing 32, 30, and 59 is thus collapsed to close the fluid path therethrough.

As shown in FIGS. 11 and 12, each of the pin means 156a, b, and c includes spring means 160 for biasing the pin means 156a, b, and c toward the normal position. In this arrangement, movement of the pin means 156a, b, and c from its normal position toward its displaced position is effected in response to operative contact with the associated cam members 138a, b, and c. This contact is, in turn, occasioned by rotation of the cam plate 132 in response to the control handle means 126.

Reference is now made to FIG. 14 and a Table which shows how the assembly 10 in any of the illustrated embodiments can be operated to handle complex, repetitive valving functions, such as those associated with a normal plasmapheresis operation. The sites of the crimping means 80 associated with the recipient tubing 59 and the first and second auxiliary tubing 30 and 32 in each of the illustrated embodiments are respectively identified as sites A, B, and C in the Table, as well as in FIGS. 5, 7, and 9. The letter "X" in the Table signifies that the tubing at the associated site is in a collapsed or occluded condition as heretofore described, and the letter "O" signifies that the tubing at the associated site is in an open or nonoccluded position.

When the control assembly 10 disposed in the PRIME mode, the tubing 59 at site A is opened, and the tubings 30 and 32 at sites B and C are collapsed. With all of the roller clamps 68, 70 and 72 associated with the recipient set 58 (which, as before explained, is preferably attached to the manifold 34 prior to its being engaged in the spring clip 92) initially closed, the spiked end portion 63 of one of the inlet lines 62 can be inserted into the outlet port of a conventional saline or similiar I.V. solution container 162 (shown in phantom lines in FIG. 3). The roller clamp 68 can then be opened to prime the filter/drip chamber 60 and establish flow of saline from the container 62 through the manifold 34 via the open tubing 59 (site A). Any flow of saline into the containers 18 and 20 is blocked by virtue of closure of the tubings 30 and 32 (at respective sites B and C).

Once the plasmapheresis assembly 16 has been primed, the venipuncture can now be made. The assembly 10 can next be disposed in the DRAW #1 mode. In this mode, the tubings 32 and 59 at sites A and C are collapsed, and the tubing 30 at site B is open to direct blood from the donor into the first container 18.

After a unit of whole blood has been collected in the first container 18, the first auxiliary tubing 30 is sealed closed downstream of the manifold 34, such as by the use of a spaced apart pair of hand seal clips (not shown), or by the formation of a hermetic, snap-apart seal using a Hematron ® dielectric sealer (also not shown), sold by the Fenwal Division of Travenol Laboratories, Inc. The auxiliary tubing 30 can be thereafter severed between the hand seal clips or along the snap-apart seal. The first container 18 is then separated from the plasmapheresis assembly 16.

The first container 18 is placed in a centrifugation device (not shown) to separate the whole blood into plasma and red cells. The unit of plasma is expressed from the container 18 by known manual or automatic means and collected for fractionation, leaving red cells in the container 18.

During the time the whole blood in the first container 18 is being processed, it is desirable to introdue a flow of saline or similar I.V. solution through the manifold 34 and the primary tubing 24 to flush traces of blood from the flow paths and to maintain the patency of the needle 26. To accomplish this, the assembly 10 is placed into the IRRIGATE mode, opening the tubing 59 at site A and closing the tubings 30 and 32 at sites B and C.

In the next step of the procedure (as shown in phantom lines in FIG. 3), the spike end portion 65 of another one of the inlet lines 64 is inserted into an outlet port 164 of the first container 18. The outlet ports 164 of each container includes a normally closed membrane 166 (see FIGS. 1 and 3) which is pierced by the spiked end portion 65 to open the port 164.

The assembly 10 is now placed into the REINFUSE #1 mode, which opens the tubing 59 at site A and collapses the tubing 30 and 32 at sites B and C. The roller clamp 68 is closed and the roller clamp 70 is opened. Red cells in the container 18 are returned to the donor through the manifold 34 and the primary tubing 59.

After the red cells in the first container 18 have been returned to the donor, the heretofore open roller clamp 70 (controlling red cell flow) is closed, and the heretofore closed roller clamp 68 (controlling saline flow) is opened to again flush traces of red cells from the main passage and the primary tubing.

The next step in the plasmapheresis procedure is to collect an additional unit of whole blood in the second collection container 20. In this step, the assemlby 10 is placed in the DRAW #2 mode which collapses the tubings 59 and 30 at sites A and B and opens the tubing 32 at site C so that blood can flow from the donor into the second container 20.

After whole blood has been collected in the second container 20, the second auxiliary tubing 32 is sealed closed downstream of the manifold 34 by the use of the pair of hand seal clips or the formation of a hermetic, snap-apart seal. The second auxiliary tubing 32 is then severed at the closure point to separate the second container 20 from the assembly 16 for processing.

While the whole blood in the separated second container is being processed, the assembly 10 is again placed in the IRRIGATE mode, heretofore described, to allow a flow of saline through the manifold 34 into the donor's arm.

The final step of the procedure begins. The spiked end portion 67 of the remaining inlet line 66 of the recipient set 58 is inserted into the outlet port 164 of the second container 20 (shown in phantom lines in FIG. 3), thereby opening the associated membrane 166. The assembly 10 is placed in the REINFUSE #2 mode opening the tubing 59 at site A and collapsing the tubing 30 and 32 at respective sites B and C. Red cells in the second container 20 are returned to the donor by opening the appropriate roller clamp 72 (controlling red cell flow) and closing the roller clamp 68 (terminating the flow of saline). Plasmapheresis procedure is then concluded.

In the embodiment shown in FIGS. 9 through 12, the various operational modes can be inscribed on the control handle means 126 for the convenience of the operator. When the control handle means 126 is disposed in the LOAD position shown in FIG. 13, the tubings 59, 30, and 32 at sites A, B, and C are all open, and the door 122 can be opened to secure the manifold 34 into the housing 116 prior to a procedure or to remove the manifold 34 after the procedure.

From the foregoing, it can be appreciated that the flow control assembly 10 obviates the need for a plurality of hemostats, roller clamps, or the like. The assembly 10 permits complex, repetitive valving functions to be made to establish a plurality of flow modes, all from a convenient, centralized location. The assembly 10 performs these valving functions in a straightforward manner, without introducing complicated, unwieldy, or leak-prone devices into the flow system. The assembly 10 is extremely adaptable and can be readily incorporated into virtually any fluid system, regardless of the complexity of the system or the complexity of the valving functions required to operate the system.

Various of the features of the invention are set forth in the following claims.

I claim:

1. A flow control assembly for flexible fluid conduits comprising
   first means including a fluid manifold defining a fluid pathway and including means for attaching two or more flexible fluid conduits to said manifold for establishing flow communications between the attached conduits, and
   second means releasably attachable to said fluid manifold and operative, when so attached, for selectively crimping at least one of the conduits attached to said fluid manifold to thereby block said flow communication through said fluid manifold.

2. An assembly according to claim 1 wherein said second means includes
   a frame,
   attachment means on said frame for releasably engaging said fluid manifold, and
   means on said frame operative, when said fluid manifold is engaged on said frame, for selectively crimping at least one of the conduits attached to said fluid manifold.

3. An assembly according to claim 2
   wherein said frame includes a base and sidewalls attached to said base, said base and sidewalls peripherally defining an interior area, and
   wherein said attachment means is carried by said base for engaging said fluid manifold within the confines of said interior area.

4. An assembly according to claim 3
   wherein said sidewalls includes means defining openings in said sidewalls corresponding in number with the number of flexible conduits attached to said fluid manifold and situated to accommodate the passage of the fluid conduits from said fluid manifold outwardly beyond said frame.

5. An assembly according to claim 4
   wherein said crimping means includes means defining a notch associated with one or more of said openings for selectively engaging and crimping a portion the fluid conduit passing through said opening.

6. An assembly according to claim 3 or 4
   wherein said crimping means includes at least one clamping means disposed on said base intermediate said attachment means and a facing sidewall, said clamping means being operative for movement between a first position generally spaced from one of the conduits attached to said fluid manifold and a second position pressing against and occluding the one conduit.

7. An assembly according to claim 6
   wherein said clamping means includes means for biasing said clamping means toward said second position and means for releasably locking said clamping means in said first position against the action of said biasing means.

8. An assembly according to claim 6
   wherein said clamping means includes
   a fixed member, and
   a movable member facing said fixed member and operatively movable between said first position, in which said movable member is disposed away from said fixed member to permit the passage of the one conduit therebetween, and said second position, in which said movable member is disposed against said fixed member to press against and occlude the one conduit passing therebetween.

9. An assembly according to claim 8 wherein said clamping means includes means for biasing said movable member toward said second position and means for releasably locking said movable member in said first position against the action of said biasing means.

10. An assembly according to claim 2 wherein said attachment means includes a spring clip operative for releasably receiving said fluid manifold.

11. An assembly according to claim 1 wherein said second means includes
a housing having spaced walls defining an interior area and including a door movable between in open position permitting access into said interior area and a closed position blocking said access,
means for releasably attaching said fluid manifold within said interior area when said door is in said open position,
fluid control means carried within said interior area and being operatively movable for selectively crimping at least one of the conduits attached to said fluid manifold,
movable control handle means carried by said door,
linkage means for connecting said control handle means with said fluid control means when said door is in said closed position to effect movement of said fluid control means in response to movement of said control handle means.

12. An assembly according to claim 11 wherein said fluid control means includes
movable plate means disposed adjacent to the conduits attached to said first means,
pin means disposed intermediate said plate means and at least one of the conduits and movable between a normal position and a displaced position, said pin means being operative during said movement from said normal position toward said displaced position for pressing against and collapsing an area of the associated conduits to obstruct the flow of fluid therethrough, and
cam means operatively connecting said plate means with said pin means for moving said pin means between said normal and displaced positions in response to movement of said plate means, and
wherein said linkage means operatively connects said control handle means with said plate means.

13. A plasmapheresis assembly comprising
primary conduit means including, at one end thereof, a phlebotomy needle,
first and second blood collection containers,
first and second auxiliary conduit means respectively attached in flow communication with said collection containers,
a fluid manifold interconnecting said primary conduit means with said first and second auxiliary conduit means, and
flow control means releasably attachable to said fluid manifold and operative, when so attached, for individually and selectively crimping each of said auxiliary conduit means to thereby block fluid communication between said primary conduit means and each of said auxiliary conduit means.

14. A plasmapheresis assembly comprising
primary conduit means including, at one end thereof, a phlebotomy needle,
first and second blood collection containers,
first and second auxiliary conduit means respectively attached in fluid communication with said collection containers,
a fluid manifold interconnecting said primary conduit means and said first and second auxiliary conduit means, said manifold including
a main passage having an end attached in flow communication with said primary conduit means and an end normally open to communication with the atmosphere and accommodating attachment to a recipient set having a length of flexible tubing for conducting fluids into said main passage,
a pair of branch passages each communicating with said main passage intermediate said ends thereof and attached in flow communication with a respective one of said first and second auxiliary conduit means, and
plug means removably insertable into said open end of said main passage for sealing said open end while simultaneously blocking flow communication between said branch passages through said main passage,
flow control means releasably attachable to said fluid manifold and operative, when so attached, for individually and selectively crimping each of said first and second auxiliary conduit means to thereby block fluid communication between said primary conduit means and each of said auxiliary conduit means.

15. A plasmapheresis assembly according to claim 14 wherein said flow control means is operative, when attached to said fluid manifold, for selectively crimping a portion of the flexible tubing of the recipient set attached to said main passage end to thereby block fluid communication therethrough.

16. A plasmapheresis assembly according to claim 13 or 14 wherein said second means includes
a frame,
attachment means on said frame for releasably engaging said first means, and
means on said frame operative, when said first means is engaged on said frame, for selectively crimping at least one of the conduits attached to said first means.

17. A plasmapheresis assembly according to claim 16 wherein said frame includes a base and sidewalls attached to said base and peripherally defining an interior area, and
wherein said attachment means is carried by said base for engaging said first means within the confines of said interior area.

18. A plasmapheresis assembly according to claim 17 wherein said sidewalls includes means defining openings in said sidewalls corresponding in number with the number of flexible conduits and situated to accommodate the passage of the fluid conduits from said first means outwardly beyond said frame.

19. A plasmapheresis assembly according to claim 18 wherein said crimping means includes means defining a notch associated with one or more of said openings for selectively engaging and crimping a portion the fluid conduit passing through said opening.

20. A plasmapheresis assembly according to claim 18 wherein said crimping means includes at least one clamping means disposed on said base intermediate said attachment means and a facing sidewall, said clamping means being operative for movement between a first position generally spaced from one of the conduits attached to said first means carried by said attachment means and a second position pressing against and occluding the one conduit.

21. A plasmapheresis assembly according to claim 20 wherein said clamping means includes means for biasing said clamping means toward said second position and means for releasably locking said clamping means in said first position against the action of said biasing means.

22. A plasmapheresis assembly according to claim 20 wherein said clamping means includes a fixed member, and a movable member facing said fixed member and operatively movable between said first position, in which said movable member is disposed away from said fixed member to permit the passage of the one conduit therebetween, and said second position, in which said movable member is disposed against said fixed member to press against and occlude the one conduit therebetween.

23. A plasmapheresis assembly according to claim 22 wherein said clamping means includes means for biasing said movable member toward said second position and means for releasably locking said movable member in said first position against the action of said biasing means.

24. A plasmapheresis assembly according to claim 13 or 14 wherein said second means includes a housing having spaced walls defining an interior area and including a door movable between in open position permitting access into said interior area and a closed position blocking said access, means for releasably attaching said first means within said interior area when said door is in said open position, fluid control means carried within said interior area and being operatively movable for selectively crimping at least one of the conduits attached to said first means, movable control handle means carried by said door, linkage means for connecting said control handle means with said fluid control means when said door is in said closed position to effect movement of said fluid control means in response to movement of said control handle means.

25. A plasmapheresis assembly according to claim 24 wherein said fluid control means includes movable plate means disposed adjacent to the conduits attached to said first means, pin means disposed intermediate said plate means and at least one of the conduits and movable between a normal position and a displaced position, said pin means being operative during said movement from said normal position toward said displaced position for pressing against and collapsing an area of the associated conduits to obstruct the flow of fluid therethrough, and cam means operatively connecting said plate means with said pin means for moving said pin means between said normal and displaced positions in response to movement of said plate means, and wherein said linkage means operatively connects said control handle means with said plate means.

26. A plasmapheresis assembly according to claim 13 or 14 wherein said flow control means includes spring clip means for releasably receiving said fluid manifold.

27. A plasmapheresis assembly according to claim 13 or 14 wherein said flow control means includes means for attaching said flow control means to the wrist of a donor.

28. A flow control assembly for flexible fluid conduits comprising first means attachable to two or more flexible fluid conduits and operative fror establishing flow communication between the attached conduits, and second means including a frame including, a base and sidewalls attached to said base, said base and sidewalls peripherally defining an interior area, means defining openings in said sidewalls corresponding in number with the number of flexible conduits for accommodating the passage of the fluid conduits from said first means outwardly beyond said frame, attachment means carried by said base for releasably engaging said first means within the confines of said interior area with the fluid conduits passing outwardly through said openings, and crimping means defining a notch associated with one or more of said openings for selectively engaging and crimping a portion the fluid conduit passing through said opening.

* * * * *